United States Patent
Dereume et al.

(10) Patent No.: US 6,309,413 B1
(45) Date of Patent: Oct. 30, 2001

(54) EXPANDABLE SUPPORTIVE ENDOLUMINAL GRAFTS

(75) Inventors: Jean-Pierre Georges Emile Dereume, Brussels (BE); David C. MacGregor; Leonard Pinchuk, both of Miami, FL (US)

(73) Assignee: Corvita Corporation, Miami, FL (US)

( * ) Notice: Subject to any disclaimer, the term of this patent is extended or adjusted under 35 U.S.C. 154(b) by 0 days.

(21) Appl. No.: 09/595,700

(22) Filed: Jun. 16, 2000

Related U.S. Application Data (63) Continuation of application No. 09/340,805, filed on Jun. 28, 1999, now Pat. No. 6,165,212, which is a continuation of application No. 08/966,268, filed on Nov. 7, 1997, now Pat. No. 5,948,018, which is a division of application No. 08/594,421, filed on Jan. 31, 1996, now Pat. No. 5,723,004, which is a continuation of application No. 08/140,245, filed on Oct. 21, 1993, now abandoned.

(51) Int. Cl.⁷ ...................................................... A61F 2/00
(52) U.S. Cl. .......................................... 623/1.13; 623/1.44
(58) Field of Search .................................... 623/1.13, 1.44

(56) References Cited

U.S. PATENT DOCUMENTS

| | | |
|---|---|---|
| 3,700,380 | 10/1972 | Kitrilakis . |
| 4,173,689 | 11/1979 | Lyman et al. ............................ 521/64 |
| 4,286,341 | 9/1981 | Greer et al. . |
| 4,323,525 | 4/1982 | MacGregor ............................. 264/24 |
| 4,459,252 | 7/1984 | MacGregor ........................... 264/56.9 |
| 4,475,972 | 10/1984 | Wong .................................. 156/167 |
| 4,512,338 | 4/1985 | Balko et al. ........................... 128/1 R |
| 4,580,568 | 4/1986 | Gianturco .............................. 128/345 |
| 4,604,762 | 8/1986 | Robinson . |
| 4,655,771 | 4/1987 | Wallsetn ..................................... 623/1 |
| 4,712,553 | 12/1987 | MacGregor ........................ 128/355.5 |
| 4,728,328 | 3/1988 | Hughes et al. . |
| 4,731,073 | 3/1988 | Robinson .................................. 623/1 |
| 4,733,665 | 3/1988 | Palmaz .................................. 128/343 |
| 4,738,740 | 4/1988 | Pinchuk et al. ........................ 156/167 |

(List continued on next page.)

FOREIGN PATENT DOCUMENTS

| | | |
|---|---|---|
| 3918736 | 12/1990 | (DE) . |
| 0 578 998 B1 | 1/1994 | (DE) . |
| 79 3020 40.5 | 4/1980 | (EP) . |
| 461791 | 12/1991 | (EP) . |
| 913 04988.8 | 12/1991 | (EP) . |
| 539237 | 4/1993 | (EP) . |
| 551179 | 7/1993 | (EP) . |
| 621015 | 10/1994 | (EP) . |
| 1205743 | 9/1970 | (GB) . |
| 2115776 | 9/1983 | (GB) . |

(List continued on next page.)

OTHER PUBLICATIONS

European Search Report, Application No. 00303472.5 dated Aug. 30, 2000.

G. J. Wilson et al., "A Self Expanding Bifurcated Endovascular Graft for Abdominal Aortic Aneurysm Repair"; Asaio Journal, U.S. J.B. Lippincott Co., vol. 42, No. 5, Sep. 1, 1996, pp. M386–M393.

*Primary Examiner*—Corrine McDermott
*Assistant Examiner*—Thomas C. Barrett
(74) *Attorney, Agent, or Firm*—Ratner & Prestia (57) ABSTRACT

An endoluminal graft which is both expandable and supportive is provided either in a longitudinal form or in a bifurcated form. The graft expands between a first diameter and a second, larger diameter. The support component is an expandable stent endoprosthesis. A cover, liner, or a liner, or both a cover and a liner are applied to the endoprosthesis in the form of a stretchable wall material that is porous, elastomeric and biocompatible in order to allow normal cellular invasion upon implantation, without stenosis, when the expandable and supportive graft is at its second diameter. Preferably, the elastomeric wall material is a polycarbonate urethane.

5 Claims, 3 Drawing Sheets

U.S. PATENT DOCUMENTS

| | | |
|---|---|---|
| 4,776,337 | 10/1988 | Palmaz . |
| 4,800,882 | 1/1989 | Gianturco ............................. 128/343 |
| 4,816,028 | 3/1989 | Kapadia et al. ......................... 623/1 |
| 4,820,298 | 4/1989 | Leveen et al. . |
| 4,851,009 | 7/1989 | Pinchuk . |
| 4,873,308 | 10/1989 | Coury et al. ........................... 528/75 |
| 4,878,908 | 11/1989 | Martin et al. ............................. 623/1 |
| 4,950,227 | 8/1990 | Savin et al. ................................ 604/8 |
| 4,954,126 | 9/1990 | Wallsten ................................. 600/36 |
| 4,994,071 | 2/1991 | MacGregor .......................... 606/194 |
| 5,019,090 | 5/1991 | Pinchuk ................................ 606/194 |
| 5,104,399 | 4/1992 | Lazarus ..................................... 623/1 |
| 5,116,360 | 5/1992 | Pinchuk et al. .......................... 623/1 |
| 5,123,917 | 6/1992 | Lee . |
| 5,133,742 | 7/1992 | Pinchuk . |
| 5,152,782 | 10/1992 | Kowligi et al. . |
| 5,156,620 | 10/1992 | Pigott ....................................... 623/1 |
| 5,171,262 | 12/1992 | MacGregor ............................... 623/1 |
| 5,195,984 | 3/1993 | Schatz ................................... 606/195 |
| 5,211,683 * | 5/1993 | Maginot .............................. 128/898 |
| 5,229,431 | 7/1993 | Pinchuk . |
| 5,236,447 | 8/1993 | Kubo et al. ............................... 623/1 |
| 5,282,823 | 2/1994 | Schwartz et al. .................... 606/198 |
| 5,290,305 | 3/1994 | Ionue ................................... 606/191 |
| 5,330,500 | 7/1994 | Song ..................................... 606/198 |
| 5,354,308 | 10/1994 | Simon et al. ......................... 606/198 |
| 5,356,423 | 10/1994 | Tihon et al. .......................... 606/194 |
| 5,360,443 | 11/1994 | Barone et al. ........................ 606/191 |
| 5,385,580 | 1/1995 | Schmitt ..................................... 623/1 |
| 5,443,499 | 8/1995 | Schmitt ..................................... 623/1 |
| 5,653,747 | 8/1997 | Dereume . |
| 5,683,449 | 11/1997 | Marcade ....................................... 1/1 |
| 5,723,004 | 3/1998 | Dereume et al. . |
| 5,871,538 | 2/1999 | Dereume . |

FOREIGN PATENT DOCUMENTS

| | | |
|---|---|---|
| 2189150 | 10/1987 | (GB) . |
| 9206734 | 4/1992 | (WO) . |
| 92 009246 | 6/1992 | (WO) . |
| 9401056 | 1/1994 | (WO) . |
| WO 95 13033 | 5/1995 | (WO) ............................................ 1/1 |

* cited by examiner

EXPANDABLE SUPPORTIVE ENDOLUMINAL GRAFTS

This application a continuation of application U.S. Ser. No. 09/340,805 filed Jun. 28, 1999, now U.S. Pat. No. 6,165,212, which is a continuation of application U.S. Ser. No. 08/966,268, filed Nov. 7, 1997, now U.S. Pat. No. 5,984,018, which is a divisonal of application Ser. No. 08/594,421, filed Jan. 31, 1996, now U.S. Pat. No. 5,723, 004, which is a continuation of application U.S. Ser. No. 08/140,245, filed Oct. 21, 1993, abandoned.

DESCRIPTION

BACKGROUND AND DESCRIPTION OF THE INVENTION

This invention generally relates to supportive endoluminal grafts which have the ability to be delivered transluminally and expanded in place to provide a graft that is endoluminally positioned and placed, with the aid of an appropriate catheter, and that remains so placed in order to both repair a vessel defect and provide lasting support at the location of the graft. More particularly, the graft combines into a single structure both an expandable luminal prosthesis tubular support component and an elastomeric graft component wherein the material of the graft substantially covers either the internal, the external or both of the internal and external surfaces of the expandable tubular support component. When desired, the expandable supportive luminal graft takes on a bifurcated structure for repair and support of vessel locations at or near branching sites. The graft component is stretchable or elastomeric and does not substantially inhibit expansion of the tubular support component while simultaneously exhibiting porosity which facilitates normal cellular growth or invasion thereinto of tissue from the body passageway after implantation.

Elastomeric vascular grafts are known to be made by various methods. Included are methods which incorporate electrostatic spinning technology such as that described by Annis et al. in "An Elastomeric Vascular Prosthesis", *Trans. Am. Soc. Artif. Intern. Organs*, Vol. XXIV, pages 209–214 (1978) and in U.S. Pat. No. 4,323,525. Other approaches include elution of particulate material from tubular sheeting, such as by incorporating salts, sugars, proteins, water-soluble hydrogels, such as polyvinyl pyrrolidone, polyvinyl alcohol, and the like, within polymers and then eluting the particulate materials by immersion in water or other solvent, thereby forming pores within the polymer. Exemplary in this regard is U.S. Pat. No. 4,459,252, incorporated by reference hereinto. Another approach involves the forming of pores in polymers by phase inversion techniques wherein a solventized polymer is immersed in another solvent and the polymer coagulates while the polymer solvent is removed. Also known are spinning techniques such as those described in U.S. Pat. No. 4,475,972. By that approach, a polymer such as a polyurethane in solution is extruded as fibers from a spinnerette onto a rotating mandrel. The spinnerette system reciprocates along a path which is generally parallel to the longitudinal axis of the mandrel and at a controlled pitch angle. The result is a non-woven structure where each fiber layer is bound to the underlying fiber layer.

Also known are stent devices, which are placed or implanted within a blood vessel or other body cavity or vessel for treating occlusions, stenoses, aneurysms, disease, damage or the like within the vessel. These stents are implanted within the vascular system or other system or body vessel to reinforce collapsing, partially occluded, weakened, diseased, damaged or abnormally dilated sections of the vessel. At times, stents are used to treat disease at or near a branch, bifurcation and/or anastomosis. This runs the risk of compromising the degree of patency of the primary vessel and/or its branches or bifurcation, which may occur as a result of several problems such as displacing diseased tissue, vessel spasm, dissection with or without intimal flaps, thrombosis and embolism.

One common procedure for implanting a stent is to first open the region of the vessel with a balloon catheter and then place the stent in a position that bridges the diseased portion of the vessel. Various constructions and designs of stents are known. U.S. Pat. No. 4,140,126 describes a technique for positioning an elongated cylindrical stent at a region of an aneurysm to avoid catastrophic failure of the blood vessel wall, the stent being a cylinder that expands to an implanted configuration after insertion with the aid of a catheter. Other such devices are illustrated in U.S. Pat. No. 4,787,899 and U.S. Pat. No. 5,104,399. U.S. Pat. No. 4,503,569 and U.S. Pat. No. 4,512,338 show spring stents which expand to an implanted configuration with a change in temperature. It is implanted in a coiled configuration and then heated in place to cause the material of the spring to expand. Spring-into-place stents are shown in U.S. Pat. No. 4,580,568. U.S. Pat. No. 4,733,665 shows a number of stent configurations for implantation with the aid of a balloon catheter. U.S. Pat. No. 5,019,090 shows a generally cylindrical stent formed from a wire that is bent into a series of tight turns and then spirally wound about a cylindrical mandrel to form the stent. When radially outwardly directed forces are applied to the stent, such as by the balloon of an angioplasty catheter, the sharp bends open up and the stent diameter enlarges. U.S. Pat. No. 4,994,071 describes a bifurcating stent having a plurality of wire loops that are interconnected by an elongated wire backbone and/or by wire connections and half hitches.

Stents themselves often do not encourage normal cellular invasion and can lead to undisciplined development of cells in the stent mesh, with rapid development of cellular hyperplasia. Grafts alone do not provide adequate support in certain instances. Copending application of Jean-Pierre Dereume, Ser. No. 112,774, entitled "Luminal Graft Endoprostheses and Manufacture Thereof" describes grafts that have the ability to carry out dilatation and/or support functions. An expandable tubular support component and an elastomeric graft component are combined into a single device wherein the graft material is secured to either or both of the internal and external surfaces of the expandable support component. The graft material is produced by a spinning technique such as that described in U.S. Pat. No. 4,475,972. Also, luminal endoprostheses with an expandable coating on the surface of external walls of radially expandable tubular supports are proposed in U.S. Pat. No. 4,739, 762 and U.S. Pat. No. 4,776,337. In these two patents, the coating is made from thin elastic polyurethane, Teflon film or a film of an inert biocompatible material. A. Balko et al., "Transfemoral Placement of Intraluminal Polyurethane Prosthesis for Abdominal Aortic Aneurysm", *Journal of Surgical Research*, 40, 305–309, 1986, and U.S. Pat. No. 5,019,090 and U.S. Pat. No. 5,092,877 mention the possibility to coat stent materials with porous or textured surfaces for cellular ingrowth or with non-thrombogenic agents and/or drugs.

By the present invention, grafts which are expandable and supportive are provided that expand from a first diameter to a second diameter which is greater than the first. When it is at its first diameter, the expandable supportive graft is of a size and shape suitable for insertion into the desired body passageway. The material of the graft is subtantially inert and has a generally cylindrical cover and/or lining generally over the outside and/or inside surface of the expandable supportive component. The cover and/or lining is especially advantageous because it is elastomeric and porous to encourage desirable growth of tissue thereinto in order to assist in non-rejecting securement into place and avoidance of stenosis development. When a bifurcated expandable supportive luminal graft is desired, the porous, elastomeric liner and/or cover is secured over a bifurcated expandable understructure. The material must be elastomeric enough to allow for expansion by up to about 2 to 4 times or more of its unexpanded diameter.

It is a general object of the present invention to provide an improved luminal graft that is expandable in place and, once expanded, is self-supporting.

Another object of this invention is to provide biocompatible grafts that are expandable in vivo and are supportive once so expanded.

Another object of the present invention is to provide an improved expandable reinforced graft that is delivered by way of a balloon catheter or similar device, whether in tubular or bifurcated form, which facilitates good tissue ingrowth.

Another object of this invention is to provide an improved endoluminal graft which fully covers diseased or damaged areas for carrying out luminal repairs or treatments.

Another object of the present invention is to provide an improved endoluminal graft wherein the endoprothesis is substantially enclosed within biocompatible elastomeric material which is presented to the surrounding tissue and blood or other body fluid.

Another object of this invention is to provide an expandable, supportive graft that can be tailored to meet a variety of needs, including a single graft designed to address more than a single objective.

Another object of the present invention is to provide a self-expanding reinforced graft that is delivered in its elongated and compressed state from within a tubular member and deployed by moving same out of the tubular member.

These and other objects, features and advantages of this invention will be clearly understood through a consideration of the following detailed description.

BRIEF DESCRIPTION OF THE DRAWINGS

The invention will be further elucidated in the following description with reference to the drawings, in which.

DESCRIPTION OF THE PARTICULAR EMBODIMENTS

The entire disclosure of U.S. patent application Ser. No. 09/340,805 filed Jun. 28, 1999 is expressly incorporated by reference herein.

Figure 1:
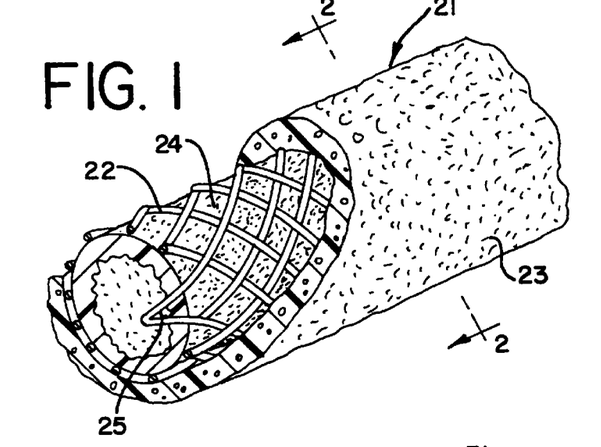
FIG. 1 is a perspective view, partially cut away, of an expandable supportive endoluminal graft in accordance with the invention.
Figure 2:
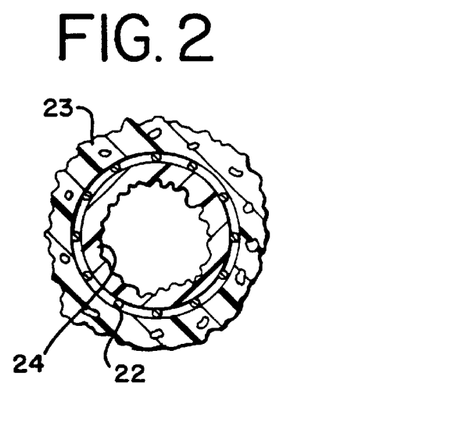
FIG. 2 is a cross-sectional view along the line 2—2 of FIG. 1.

An embodiment of the expandable supportive luminal graft is generally illustrated in FIG. 1 at 21. This embodiment includes a braided tubular support component having generally helically wound rigid but flexible strand or wire elements, some of which have the same direction of winding but are axially displaced from one another, and others of which cross these windings and are also axially displaced with respect to each other. The actual structure can be generally braided as illustrated in Wallsten U.S. Pat. No. 4,655,771, incorporated by reference hereinto, or as found in self-expanding braided flat wire Wallstent® devices. Both a cover 23 and a liner 24 are illustrated in FIGS. 1 and 2. Either cover 23 or liner 24 can be omitted if there is no desire to substantially encapsulate the tubular support component 22.

With more particular reference to the illustrated cover 23 and liner 24, when included, they are formed by an electrostatic spinning process in this illustrative embodiment. Details regarding electrostatic spinning techniques in general are found in Bornat U.S. Pat. No. 4,323,525 and in Bornat European patent publication No. 9,941, as well as in the Annis et al. article discussed hereinabove, the disclosures of which are incorporated by reference hereinto. With further reference to the application of this technology to the expandable supportable luminal grafts of the present invention, random pattern filaments are formed and electrostatically directed toward a charged mandrel in order to form a random pattern of electrostatically generally cross-linked filaments which take on the configuration of a mat having a cylindrical shape. The filament diameters are particularly fine, as is the pore size of the mat so constructed. A typical range of filament diameters is between about 0.5 micron and about 5 microns, and a typical pore size of the electrostatically spun fiber is between about 3 microns and about 20 microns.

Liner 24 is formed directly on the rotating mandrel by this electrostatic spinning procedure. Thereafter, one of the tubular support components discussed herein, such as the generally braided tubular support 22, is placed over the liner 24 still on the mandrel. In the case of the tubular support 22 in a form that is not spring loaded, this includes longitudinally extending the tubular support 22, such as by pulling one or both of its ends, which thereby decreases its diameter so that it fits snugly over the liner 24. When the generally braided tubular support 22 is of a spring-into-place type, a holddown member (not shown) is used to prevent automatic radial expansion prior to deployment. When the expandable supportive graft 21 is to include a cover 23, the mandrel is again rotated, and the electrostatic spinning is again accomplished in order to form the cover 23 directly over the tubular support 22. This will also create some bonding between the thus formed cover 23 and the liner 24 at openings between the strands or wires of the woven tubular support 22 or the like. This bonding can be facilitated by uniformly compressing the outer fibers with a soft silicone rubber sponge such that the still tacky outer fibers bond to the inner fibers thereby encapsulating the tubular support within the graft.

Bonding may also be achieved in this or other embodiments by heat welding and/or by the use of adhesives such as hot melt adhesives, primers, coupling agents, silicone adhesives, and the like, and combinations of these. Examples include aliphatic polycarbonate urethane hot melts and silicone rubber adhesives.

It is important to note that each of the cover 23 and the liner 24, when either or both are present, is made of an elastomeric material which retains its compliant properties after construction of the expandable supportive graft 21 is completed. In this regard, the graft itself is also elastomeric and compliant. Accordingly, the graft 21 is delivered transluminally, such as by being pulled down onto the balloon of a catheter and then percutaneously inserted and positioned to the location where the repair is needed. For a non-spring loaded graft, the balloon is then inflated to longitudinally contract and radially expand the graft 21 into engagement with the vessel walls. Because of the compliance of the cover 23 and/or liner 24, and because of the hoop strength of the braided tubular support 22, the graft 21 will remain in place. In the illustrated embodiment, ends 25 of the tubular support are exposed and are not covered by the cover 23. This allows the exposed end portions 25 to directly engage the vessel wall, if desired in the particular application, in order to assist in anchoring the graft 21 in place. Liner 24 also can be sized so as to not cover the exposed ends 25, or it can extend to or beyond the edge of the ends 25 when it is desired to avoid or minimize contact between the tubular support and the blood or other fluid flowing through the vessel being repaired or treated.

Alternatively, when a braided tubular support such as that illustrated in FIGS. 1 and 2 is incorporated into the graft according to the present invention in a non-spring-loaded form, transluminal delivery can be made by way of a catheter or tool having means for longitudinally compressing the endoprosthesis until it has expanded radially to the desired implanted diameter. Such equipment typically includes a member that engages one end of the endoprosthesis and another member which engages the other end of the endoprosthesis. Manipulation of proximally located controls then effects relative movement of the members toward each other in order to thereby longitudinally compress the endoprosthesis. Delivery tools for spring-loaded grafts include a sleeve that maintains the graft at its compressed diameter until the graft is positioned for deployment such as from the end of an insertion catheter to its auto-expanded state.

Figure 3:
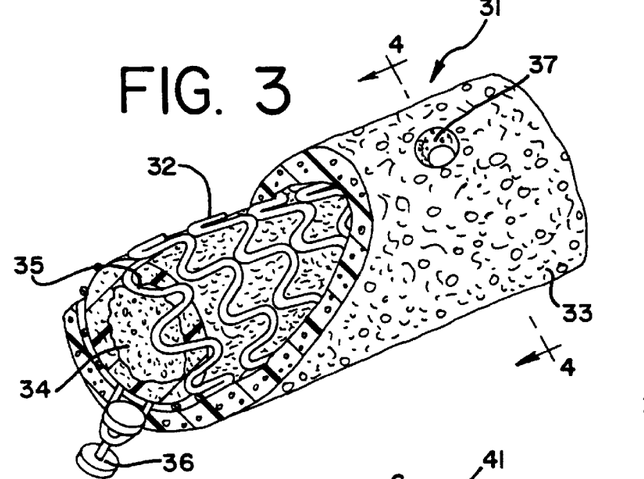
FIG. 3 is a perspective view, partially cut away, of another embodiment of the expandable supportive endoluminal graft.
Figure 4:
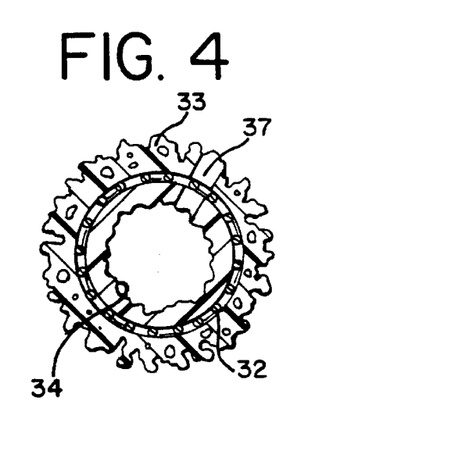
FIG. 4 is a cross-sectional view along the line 4—4 of FIG. 3.

With reference to the embodiment illustrated in FIGS. 3 and 4, an expandable supportive graft is illustrated at 31. The illustrated tubular support component 32 is constructed of sinusoidally configured wire helically wound into a tubular shape. General structures of these types are generally discussed in Pinchuk U.S. Pat. No. 5,019,090, incorporated by reference hereinto. A cover 33 can be positioned over the tubular support 32 and/or a liner 34 can positioned along its lumen. In this illustrated embodiment, the cover 33 and liner 34 are constructed of porous polymers, the pores thereof having been made by elution or extraction of salts and the like, such as described in MacGregor U.S. Pat. No. 4,459,252, incorporated by reference hereinto. Generally speaking, the porosity is determined by the size of the elutable particles as discussed herein and by the concentration of those particles as a percent by volume of a pre-elution mixture thereof with the polymer of the cover or liner. When a graft 31 having both a cover 33 and a liner 34 is prepared, a mandrel or rod is dipped into a liquid polymer having elutable particles as discussed herein dispersed therewithin. After dipping, the polymer covered rod is contacted with, such as by dipping or spraying, a solvent, for the elutable particles, such as water, thereby forming the eluted porous liner 34. Thereafter, the tubular support 32 is positioned thereover and pressed down into the liner. Then, the rod and the assembly thereon are again dipped into the mixture of polymer and elutable particles, followed by setting and contact with solvent to remove the elutable particles in order to form the eluted porous cover 33. It is also possible to directly extrude the particle-containing polymer into a tubular shape.

Elutable particles which can be used in the making of the eluted porous cover 33 and liner 34 include salts such as sodium chloride crystals, sodium carbonate, calcium fluoride, magnesium sulfate and other water-soluble materials that are readily dissolved by the utilization of water as an elution medium. Other particles that are soluble in organic solvents and the like can be substituted as desired. Further particles include sugars, proteins, and water-soluble hydrogels such as polyvinyl pyrrolidone and polyvinyl alcohol. Suitable polymer materials are as discussed elsewhere herein, the pore size being on the order of about 10 microns to about 80 microns.

As with the other embodiments, when desired, ends 35 of the support component 32 can be exposed either on one or both of its cylindrical faces in accordance with the needs of the particular repair or treatment to be carried out. With this approach, the exposed ends 35 will assist in maintaining the graft 32 in place by mechanical engagement between the exposed ends 35 and the vessel being repaired or treated and/or by tissue ingrowth. The anchoring aspect of the exposed ends of the tubular support can be enhanced by continued radial expansion of the balloon or other deployment means which will permit the exposed ends to expand radially outwardly in an amount somewhat greater than that of the rest of the expandable supportive graft and into the surrounding tissue. It is also contemplated that mechanical means can be used to assist in joining the exposed ends of this embodiment or of other embodiments to the vessel wall. An illustrative example in this regard is the use of transluminally delivered staples which can take on the appearance of rivets. Especially advantageous are staples made of an elastomeric material. Illustrated staples are shown at 36 in FIG. 3. They can be incorporated at other locations as well along the graft. One or more windows 37 can be formed through the cover and/or liner and/or tubular support in order to feed outside branch arteries or other vessels.

Figure 5:
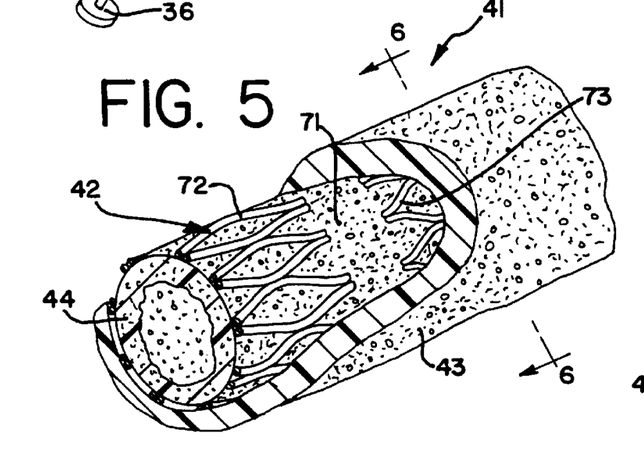
FIG. 5 is a perspective view, partially cut away, of a further embodiment of the expandable luminal graft.
Figure 6:
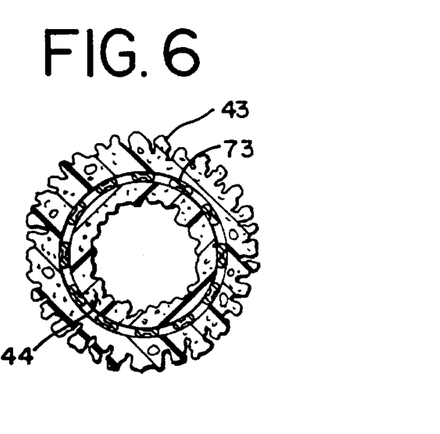
FIG. 6 is a cross-sectional view along the line 6—6 of FIG. 5.

FIGS. 5 and 6 illustrate a further embodiment of an expandable supported graft, generally designated as 41. Shown is a mesh tubular support component, generally designated as 42, such as those of the type illustrated in Palmaz U.S. Pat. No. 4,733,665, incorporated by reference hereinto. These are non-woven mesh-type cylinders or slotted tubes wherein most or all of the individual components are either integrally joined together such as by welding or are integrally formed from a single tube. The resulting endoprostheses are malleable enough so as to be expandable by a balloon of a catheter. Usually, these endoprostheses have particularly high hoop strengths.

Cover 43 and/or liner 44 are made of polymers rendered porous by phase inversion techniques. In accordance with these techniques, a polymer such as a polyurethane is dissolved in a solvent therefor, for example a water-soluble polar solvent, such as dimethyl acetamide, tetrahydrofuran and the like, in order to form what is known as a lacquer. A mandrel or rod is dipped into the lacquer. Thereafter, the dipped rod is contacted with an inversion solvent, such as by dipping in water or a mixture of alcohol and water. This inversion solvent must readily dissolve the polymer solvent of the lacquer, while at the same time being a poor solvent for the polymer. Under these conditions, the polymer coagulates and the polymer solvent of the lacquer is removed and replaced with the inversion solvent. The inversion solvent pulls the polymer solvent out of the polymer on the rod and forms particularly fine pores having a pore size on the order of about 0.5 micron to about 20 microns. The thus formed liner 44 having phase inversion pores is then dried.

Next, the tubular support component 42 is secured over the liner 44 and is preferably radially compressed onto and into the liner. Thereafter, the cover 43 having phase inversion pores is formed in accordance with the same phase inversion steps as discussed hereinabove for preparation of the liner 44. If desired, either the liner or the cover can be omitted. Cover 43 and liner 44 are thus formed in accordance with a displacing step wherein precipitating non-solvent molecules are substituted for non-precipitating solvent molecules dispersed throughout the lacquer coating. This procedure develops advantageous elastic characteristics. Further details regarding the phase inversion procedure are found in Lymann et al. U.S. Pat. No. 4,173,689, incorporated by reference hereinto.

Figures 7, 8, 9, 10:
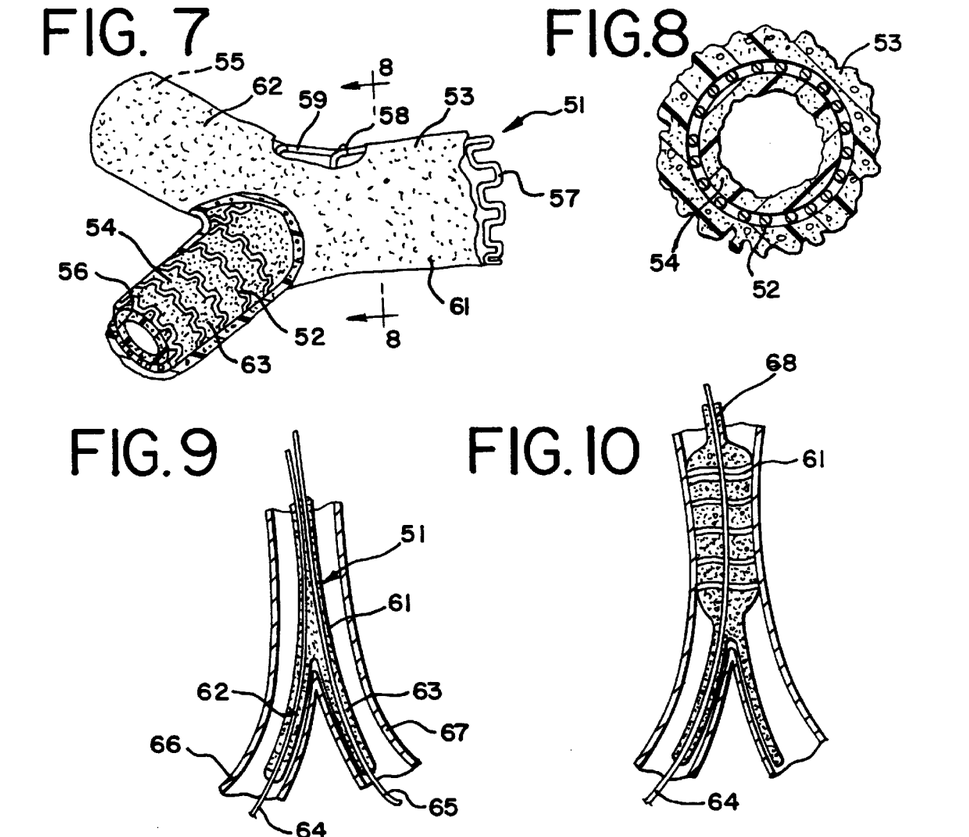
FIG. 7 is a perspective view, partially cut away, of a bifurcated expandable supportive endoluminal graft in accordance with the invention.
FIG. 8 is a cross-sectional view along the line 8—8 of FIG. 7.
FIG. 9 is a somewhat schematic view illustrating an early step in the implantation of a device such as shown in FIG. 7.
FIGS. 10, 11 and 12 are generally schematic views along the lines of FIG. 9 showing expansion of the main body and the branches of the bifurcated device.

FIGS. 7 and 8 illustrate an embodiment wherein the graft takes the form of a bifurcated expandable supportive graft, generally designated at 51. Included is a joined-ring bifurcated tubular support 52. Also shown are a bifurcated cover 53, a bifurcated lining 54 and exposed ends 55, 56, 57. This particular bifurcating graft is well-suited for insertion into a branching vessel.

The tubular support includes a plurality of rings or loops 58 connected by flexible interconnections 59. Constructional details of embodiments of the rings or loops 58 and of the flexible interconnections 59 are found in MacGregor U.S. Pat. No. 4,994,071, incorporated by reference hereinto. The flexible interconnections 59 join the rings or loops 58 into a configuration having a main body or trunk 61 and one or more branches 62. Flexible interconnections 59 extend longitudinally from the axis of each of the main body or trunk 61 and branch 62, 63. At least one such flexible interconnection joins each branch to the trunk. The loops 58 in the main body are substantially parallel to each other, and the loops 58 in each branch 62, 63 are substantially parallel to each other.

The bifurcated cover 53 and bifurcated liner 54 must each, when provided, be especially elastomeric so as to follow the expansion and contraction of the rings or loops 58 that takes place during preparation, transluminal insertion, deployment and the like. Cover 53 and liner 54 will also take on a bifurcated construction. In one embodiment, the liner and/or cover for each of the trunk 61 and branch 62, 63 are made on a cylindrical mandrel, assembled and joined, such as by suitable biocompatible adhesive, fusion, sewing, suturing or other means of joining and/or sealing. Alternatively, a Y-shaped or branched mandrel can be used. The bifurcating liner is then formed thereon by processes such as those discussed herein, including electrostatic spinning, or dipping followed by elution or phase inversion procedures much in the same manner as described herein when straight cylindrical mandrels or rods are used for constructing the non-bifurcated grafts in accordance with this invention. Fiber winding can also be practiced. Bifurcated cover 53 is made in a similar manner by application of the porous cover material over the bifurcated endoprosthesis.

With reference to the bifurcated endoprosthesis, the bifurcated cover 53 and/or bifurcated liner 54 could be made by fiber winding approaches, such as those described in Wong U.S. Pat. No. 4,475,972, the subject matter thereof being incorporated by reference hereinto. Polymer in solution is extruded into fibers from a spinnerette onto a rotating mandrel. The spinnerette is reciprocated along the longitudinal axis of the mandrel at a controlled pitch angle, resulting in a non-woven cylinder wherein each fiber layer is bound to the underlying layer. Control of the pitch angle allows for control of the compliance and kink resistance of the cover and/or liner. In an especially advantageous arrangement when using these fiber spinning techniques in forming an expandable supportive graft in accordance with the general aspects of this invention which has both a liner and a cover, the cover is physically bonded to the liner by the use of an electrostatic field to enable penetration of the cover overlay of fibers through the interstices of the support components in order to improve the bonding of the cover and/or liner fibers to each other and/or to surfaces of the support component.

With more particular reference to the deployment of the expandable supportive grafts in accordance with this invention, this is illustrated with some particularity in connection with bifurcated endoluminal grafts in FIGS. 9, 10, 11, 12 and 13. As shown in FIG. 9, two guidewires 64, 65 are inserted into the bifurcating vessel, each of them into different legs 66, 67 of the bifurcating vessel. Thereafter, the unexpanded bifurcated expandable supportive graft 51 is slipped over the proximal ends of the guidewires and routed to the branches of the blood vessel. The unexpanded bifurcated graft can be introduced from an arteriotomy proximal to the bifurcation such as from the brachial artery in the arm, or the unexpanded bifurcated graft can be introduced from the femoral artery in the leg, pushed proximally past the bifurcation and then pulled back distally into both iliacs to form the trunk and bifurcation.

The two branches 62, 63 of the graft 51 are routed separately over the guidewires 64, 65, respectively, and guided, typically with the help of a guide catheter, into the patient until the graft is positioned as shown in FIG. 9. The graft 51 is initially fixed in place as follows. One of the guidewires 65 is removed, and a balloon catheter 68 is inserted into the main body or trunk 61 and inflated to expand the trunk 61 into contact with the vessel walls. This deployment is suitable to secure the graft 51 in place at that location of the vessel.

Figure 11:
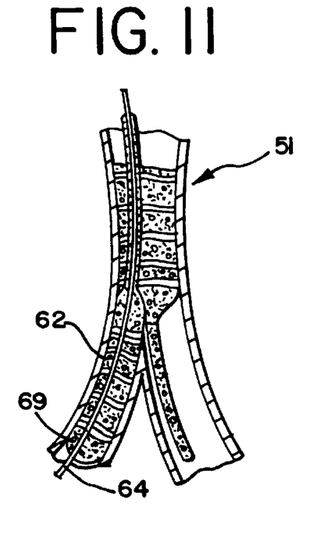
Figure 12:
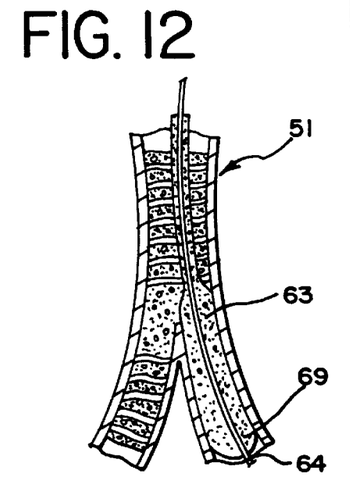
Figure 13:
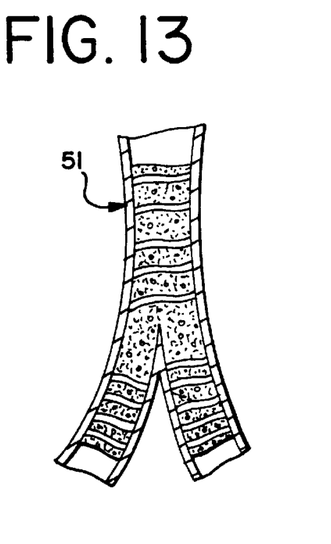
FIG. 13 shows the bifurcated supportive graft after completion of the expansion procedure.

The balloon of balloon catheter 68 is then deflated. If this balloon catheter is also suitable for use in expanding the branches 62, 63 of the graft 51, same is then inserted into an unexpanded branch 62 and radially expanded as generally shown in FIG. 11. If the balloon of catheter 68 is not suitable in this regard, then another balloon catheter 69 effects this function. FIG. 12 shows inflation of the other branch 63 of the graft 51 in a similar manner. FIG. 13 illustrates the fully deployed and expanded bifurcated support graft 51 positioned in place within the bifurcated location. Alternatively, a bifurcated dilation balloon on a bifurcated catheter (not shown) can replace the single-balloon catheter(s) 68, 69.

When the bifurcated expandable supportive graft is of a spring-into-place type, same will be placed within an overlying and bifurcated restraining guiding catheter or the like and will be passed over two guidewires and contained within the guiding catheter until proper placement within the bifurcating location. This type of bifurcated expandable supportive graft is deployed by being ejected into place by advancing a small inner catheter through the guiding catheter into contact with the bifurcating graft in accordance with the procedure generally used for spring-into-place stents.

The deployment procedures illustrated in FIGS. 9 through 13 can be characterized as prograde deployment. Retrograde deployment is also possible. The entire bifurcating graft for retrograde deployment is advanced over a single guidewire through one branch of the blood vessel past the point of bifurcation. A second guidewire is then steered down the opposite limb of the graft, and a snare is used. The snare, which is passed retrograde through the opposite vessel, is then used to pull the guidewire into place. Partial balloon inflation in the unbranched or trunk portion of the blood vessel is then used to draw the graft down into position prior to balloon dilatation of both the trunk and branched portions of the graft. Because blood flow is prograde under these circumstances, the contact between the bifurcation of the graft and the bifurcation of the blood vessel helps to prevent the graft from migrating distally, thus reducing the need for active fixation of the graft to the blood vessel.

Figure 14:
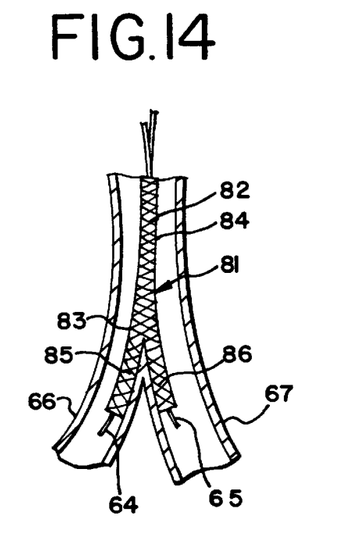
FIG. 14 illustrates another embodiment of a bifurcated expandable supportive endoluminal graft.

Another bifurcated endoprosthesis or expandable supportive graft is generally designated 81 in FIG. 14. In this embodiment, a fully independent tubular supporting component 82 is located at the trunk position of the graft 81. A bifurcated stretchable wall 83 is in contact with the independent tubular supporting component 82 as either or both of a cover or liner. In addition to being substantially coextensive with the independent tubular supporting component 82 at a trunk portion 84 thereof, the stretchable wall 83 includes at least two generally tubular stretchable branch sleeves 85, 86 which are initially devoid of a supporting component. Separate tubular supporting components 89, 90 (FIGS. 16 and 17) are also included.

Figure 15:
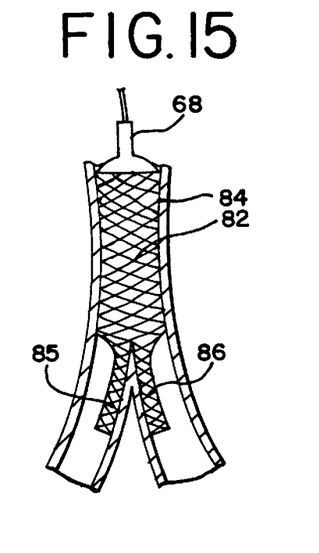
FIGS. 15, 16 and 17 illustrate implantation and assembly of the graft of FIG. 14.

Implantation of this bifurcated expandable supportive graft is depicted in FIGS. 14, 15, 16 and 17. Dual guidewires 64, 65 can be used to properly position the unexpanded bifurcated graft 81 within the bifurcating vessel as shown in FIG. 14. A balloon catheter 68 or similarly functioning device is inserted into the main body of the device so as to expand the independent tubular supporting component 82 and the trunk portion 84 of the bifurcated stretchable wall 83. This deployment initially secures the bifurcated supporting graft into place at that location of the vessel, as shown in FIG. 15. The balloon catheter is then deflated and removed or positioned for use in the next step.

Figure 16:
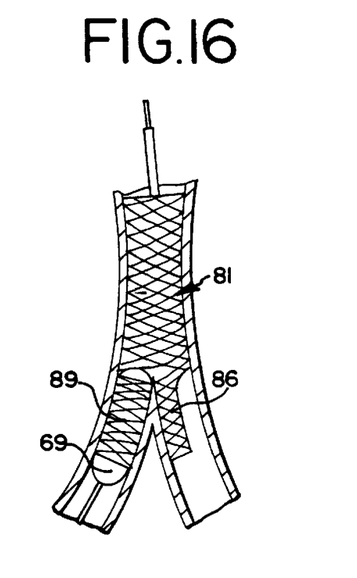
Figure 17:
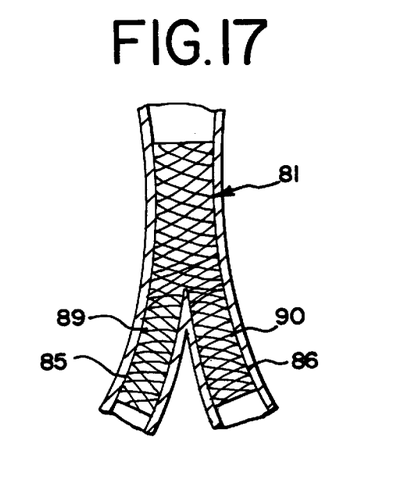

A suitable balloon catheter 69 or the like is next used to deploy and expand in place a branch tubular expandable supporting component 89, as illustrated in FIG. 16. A similar step deploys and expands in place another branch tubular expandable supporting component 90, as generally shown in FIG. 17. The bifurcated stretchable wall 83 and the expandable supporting components may be made with the materials and constructions discussed herein and may be subjected to various treatments as discussed.

A preferred use for the bifurcating endoluminal grafts discussed herein is for insertion into a branching blood vessel. Same is typically suitable for use in the coronary vasculature (the right, left common, left anterior descending, and circumflex coronary arteries and their branches) and the peripheral vasculature (branches of the carotid, aorta, femoral, popliteal arteries and the like). These bifurcated devices are also suitable for implantation into other branching vessels such as in the gastrointestinal system, the tracheobronchial tree, the biliary system, and the genitourinary system.

It will be appreciated that the expandable supportive grafts in accordance with the present invention will dilate and/or support blood vessel lesions and other defects or diseased areas, including at or in proximity to sites of vascular bifurcations, branches and/or anastomoses. The expandable supportive graft is an integral structure that incorporates the expandable support component into the wall or walls of the elastomeric graft. Covers and/or linings that make up the grafts interface with body components that facilitate normal cellular invasion without stenosis or recurrent stenosis when the graft is in its expanded, supportive orientation. The graft material is inert and biocompatible. The expandable supportive graft can be expanded from a smaller diameter insertion configuration to a larger diameter implantation configuration by the application of radially outwardly directed forces provided by expanding the endoprosthesis with a balloon catheter, using an ejection tube that allows a spring-into-place structure to be deployed from the end of a catheter into its expanded configuration, or by using a support component made of certain alloys exhibiting thermotransition characteristics by which they expand when heated, for example.

In addition to the support component structures illustrated herein, support structures include others having spring characteristics and those having a coil with circumferentially oriented fingers such as shown in Gianturco U.S. Pat. No. 4,800,882, incorporated by reference hereinto. Materials include, either alone or in combination, metals or metal alloys, polymers, carbon and ceramics. Exemplary metallic members include stainless steel, titanium, tantalum, Nitinol, Elgiloy (trade name) and NP35N (trade designation), which can provide desired degrees of springiness, malleability and/or response to temperature changes. Exemplary polymers include polyurethanes, silicone rubbers, polyether sulfones, fluoroelastomers, polyimides, polycarbonates, polyethylenes, polylactic acid, polyglycolic acid, polyacrylates, and the like and combinations and copolymers thereof which provide a variety of abilities to bioabsorb or biodegrade or to be totally inert. Any of a variety of these endoprostheses can be combined with any of a variety of the graft cover and/or liner configurations in order to tailor the expandable supportive graft to meet specific needs. Also, combinations can be obtained, such as providing phase inversion pores and salt elution pores on different locations of the graft component to take advantage of the pore size difference between these two types of graft techniques and/or to provide better tissue growth at one location than at another.

With reference to the material out of which the cover and/or liner of the grafts in accordance with the present invention are made, the material must be stretchable and/or support component so that it will follow the movement of the endoprosthesis between its fully collasped and expanded or implanted configurations. Polyurethanes are preferred. Particularly preferred is an especially crack-resistant, elastomeric and pliable polycarbonate urethane as described in Pinchuk U.S. Pat. No. 5,133,742 and U.S. Pat. No. 5,229, 431, incorporated by reference hereinto, available from Corvita Corporation under the CORETHANE® trademark. Also suitable are polycarbonate polyurethane covers and liners coated with a thin layer of silicone rubber material as described in Pinchuk U.S. Pat. No. 4,851,009, incorporated by reference hereinto.

In addition, various surface treatments can be applied to render the surfaces of the expandable supported graft more biocompatible. Included are the use of pyrolytic carbon, hydrogels and the like. The surface treatments can also provide for the elution or immobilization of drugs such as heparin, antiplatelet agents, antiplatelet-derived growth factors, antibiotics, steroids, and the like. Additionally, the coating and/or liner can be loaded with drugs such as those discussed herein, as well as lytic agents in order to provide local drug therapy.

The expandable supportive graft of the present invention is capable of being tailored to meet specific needs, depending upon the particular defect or disease being addressed, such as occlusion, stenosis, aneurysm, arteriovenosis fistula, trauma and the like, as well as upon the anatomy of the vessel. For example, it can be desirable to have the support component of the expandable supportive graft at locations other than throughout the entirety of the graft as specifically illustrated in FIGS. 1 through 4 hereof. The bifurcated graft of FIGS. 7 and 8 shows some separation along the support component, such as between the trunk 61 and the branches 62, 63. It is also possible, with the grafts in accordance with the present invention, to provide an expandable graft having its supportive property emanating from one or more support components, while thereby providing an adjoining graft cylindrical portion which is supported primarily by its close proximity to a support component which can be presented at one end, both ends, or spaced along the expandable supportive graft in accordance with invention.

Such a structure is generally illustrated in FIG. 5, wherein an adjoining graft cylindrical portion 71 is positioned between a first support component 72 and another or second support component 73. The expandable supportive graft in accordance with the present invention provides the tailorability advantage of being able to vary within a single graft the configuration, structure and properties of the support component or components of the graft. These various properties allow the expandable supportive graft to be tailored in accordance with particular needs of the disease, defect or damage being treated. For example, support may be particularly desirable at one location being treated, while a less rigid supportive area is needed at another, generally adjoining location. By the expandable supportive graft in accordance with this invention, a single graft can be deployed in order to effect two or more different functions. By achieving multiple support and/or repair functions with a single device, possible trauma to the patient is minimized by reducing the number of transluminal passages needed to address a situation that could otherwise require separate stents or grafts, each of which is separately deployed or implanted.

With further reference to the tailorability aspects, the present invention reduces the risk of compromising the patency of the passageways being treated. This is particularly true in treating lesions at or near vascular bifurcations, branches and/or anastomoses. Typical difficulties which can be avoided by the present invention include displacing of diseased tissue, vessel spasm, dissection with or without intimal flaps, thrombosis, embolism, and the like. Another suitable use is for dilating and/or supporting vascular graft bifurcations and the like. Additionally, lesions affecting vascular trifurcations can be treated. Also treatable are obstructed openings characterized by exaggerated cicatrization, abnormal cellular growth (subintimal fibromuscular hyperplasia and the like) or arterial or venous stenosis. Moreover, these supportive grafts can be used to reinforce vascular walls, weakened by pathological processes, for example, by dissection, as in the case of aneurysms. The grafts can also obliterate congenital or acquired arteriovenous communications, and they can be applied in intrahepatic portal-caval shunts. The grafts also can maintain biological pathways open, such as the digestive, biliary, pancreatic and urinary tracts, and they help to limit the intraluminal growth of pathological processes such as fibrosis or cancer.

EXAMPLE I

A vascular expandable supportive endoluminal graft was made using a 16 mm diameter, 12 cm long Wallstent® device as the support component in the following manner. A grounded 16 mm mandrel was rotated on a spinning machine at 500 RPM, and a spinnerette with 30 orifices was reciprocated along the axis of the mandrel at 13.8 inches/second while applying 40,000 volts to the spinnerette. Polycarbonate urethane, in dimethyl acetamide solution (45% solids) was extruded from the spinnerette at 0.123 ml/min, the fibers coming onto the mandrel in random fashion to form a mat-like structure having randomly shaped pores. The environment in the spinning chamber was controlled such that sufficient solvent from the urethane solution evaporated off during spinning to enable the fibers to bond to underlying fibers during each transverse of the spinnerette. After 300 passes of the spinnerette, the spinning procedure was stopped and the mandrel with the spun polycarbonate urethane mat was removed from the machine and cured at 110° C. for 16 hours. The tubular mat still on the mandrel was trimmed to the appropriate size and the Wallstent® device was sheathed over the mesh and the ends taped down. Another 10 passes of polycarbonate urethane were spun over the Wallstent® device, and the fibers, while still wet, were immediately pressed through the interstices of the Wallstent® device with a silicone rubber sponge, such that the fibers bonded to the underlying fibers of the urethane mat, thereby capturing the Wallstent® device within the urethane wall. The assembly was then cured for an additional 3 hours at 110° C., after which the assembly was removed from the mandrel. The expandable supportive endoluminal graft formed in this manner had the bulk of the urethane mesh on the inside of the stent. This endoprosthesis is suitable for repairing aortic aneurysms.

EXAMPLE II

A bifurcated aortic expandable supportive endoluminal graft is made in the following manner: An aortic trunk supportive endoluminal graft is fabricated using a 16 mm diameter, 12 cm long support component. First, a 16 mm mandrel is rotated on a spinning machine at 500 rpm, and a spinnerette with 30 orifices reciprocated along the axis of the mandrel at 13.8 inches/second. Polycarbonate urethane, in dimethyl acetamide solution (45% solids) is extruded from the spinnerette at 0.123 ml/min and wound onto the rotating mandrel such that the fibers form a 50° pitch angle in relation to the axis of the mandrel. The environment in the spinning chamber is controlled such that sufficient solvent from the urethane solution evaporates off during spinning to enable the fibers to bond to underlying fibers during each transverse of the spinnerette. The thus formed spun polycarbonate urethane mesh has a length of about 16 cm, is removed from the machine and is cured at 110° C. for 16 hours. The support component is sheathed over the mesh still on the mandrel with a 4 cm excess length of tubular mesh protruding beyond the support component. Another 10 passes of polycarbonate urethane were spun over the tubular mesh, support component, but not over the 4 cm excess length of the internal tubular mesh, and the fibers, while still wet, were immediately pressed through the interstices of the support component with a silicone rubber sponge, such that the fibers bonded to the underlying fibers of the urethane mesh, thereby capturing the support component within the urethane wall. The assembly was then cured for an additional 3 hours at 110° C., after which the assembly was removed from the mandrel. The supportive endoluminal graft formed in this manner has fiber diameters of 10 to 20 $\mu$ and pore sizes ranging from 10 to 60 $\mu$. The excess tubular mesh which protrudes from one side of the assembled endoprosthesis is then slit and sewn down the center such that the tube is bifurcated into two smaller tubes, thereby resembling a pair of short pants. The aortic trunk endoprosthesis is pulled down and sheathed on an introducer catheter, maneuvered into the aorta of a dog, via the dog's femoral artery for deployment in the abdominal aorta. Two smaller stents, of 8 mm diameter, are also pulled down onto introducer catheters and maneuvered, through each femoral artery for deployment into the "pant legs" of the aortic trunk. The resultant bifurcated endoprosthesis is for limiting further dilation of an abdominal-iliac aneurysm.

It will be understood that the embodiments of the present invention which have been described are illustrative of some of the applications of the principles of the present invention. Various modifications may be made by those skilled in the art without departing from the true spirit and scope of the invention.

What is claimed is:

1. An expandable supportive endoluminal graft comprising:
    a tubular supporting component with a longitudinal axis having a network of land areas with open areas defined between said land areas, and having an internal surface and an external surface;
    a liner constructed of an essentially inert biocompatible material, said liner applied to said internal surface;
    a cover constructed of an essentially inert biocompatible material, said cover applied to said external surface; wherein said liner is bonded to said cover at locations defined by said open areas; and
    wherein a window is formed through said liner and said cover at a location where said liner and said cover are bonded to each other.

2. The expandable supportive endoluminal graft of claim 1 wherein said liner and said cover each has a structure that allows normal cellular ingrowth from the body pathway when said expandable supportive endoluminal graft is implanted therein.

3. The expandable supportive endoluminal graft of claim 1 wherein said cover is substantially supported by said tubular supporting component.

4. An expandable supportive endoluminal graft comprising:
    a tubular supporting component with a longitudinal axis having an internal surface and an external surface, said tubular supporting component defining at least one passageway from one end of said tubular supporting component to a second end, said tubular supporting component having a network of land areas with open areas defined therebetween;
    a liner constructed of an essentially inert biocompatible material, said liner applied to said internal surface;
    a cover constructed of an essentially inert biocompatible material, said cover applied to said external surface; wherein said liner is bonded to said cover at locations defined by said open areas; and
    wherein a window is formed through said liner and said cover at a location where said liner and said cover are bonded to each other.

5. The expandable supportive endoluminal graft of claim 4 wherein said cover is substantially supported by said tubular supporting component.

* * * * *